United States Patent
Chelyapov et al.

(10) Patent No.: US 11,446,329 B2
(45) Date of Patent: Sep. 20, 2022

(54) NATURAL KILLER CELL ADOPTIVE TRANSFER THERAPY FOR THE ELIMINATION OF SENESCENT PBMCS, REDUCTION OF INFLAMMATORY CYTOKINES AND TREATMENT OF IBS

(71) Applicant: RESTEM LLC, Miami, FL (US)

(72) Inventors: Nickolas Chelyapov, Placentia, CA (US); Rafael Gonzalez, Yorba Linda, CA (US)

(*) Notice: Subject to any disclaimer, the term of this patent is extended or adjusted under 35 U.S.C. 154(b) by 545 days.

(21) Appl. No.: 16/178,369

(22) Filed: Nov. 1, 2018

(65) Prior Publication Data

US 2020/0138861 A1 May 7, 2020

Related U.S. Application Data

(60) Provisional application No. 62/580,071, filed on Nov. 1, 2017.

(51) Int. Cl.
| | | |
|---|---|---|
| *C12N 5/0783* | (2010.01) | |
| *A61K 35/17* | (2015.01) | |
| *A01N 1/02* | (2006.01) | |

(52) U.S. Cl.
CPC ............ *A61K 35/17* (2013.01); *A01N 1/0278* (2013.01)

(58) Field of Classification Search
None
See application file for complete search history.

(56) References Cited

U.S. PATENT DOCUMENTS

| | | | |
|---|---|---|---|
| 6,207,147 B1 | 3/2001 | Hiserodt | |
| 9,585,914 B2 * | 3/2017 | Dilber ................. | C12N 5/0646 |
| 11,118,165 B2 * | 9/2021 | Spanholtz ............ | C12N 5/0646 |
| 2002/0068044 A1 | 6/2002 | Klingemann | |
| 2018/0015123 A1 * | 1/2018 | Choi ...................... | A61K 35/17 |
| 2021/0228632 A1 * | 7/2021 | Jongen ..................... | A61P 1/04 |

FOREIGN PATENT DOCUMENTS

WO WO2012/069369 9/2012

OTHER PUBLICATIONS

Davis, Natural Killer Cell Adoptive Transfer Therapy: Exploiting the First Line of Defense Against Cancer, Cancer J. Nov.-Dec. 2015;21(6):486-491, USA.
Katayoun, The Application of Natural Killer Cell Immunotherapy for the Treatment of Cancer, Front Immunol 2015;6:578, USA.
Besser, Development of Allogeneic NK Cell Adoptive Transfer Therapy in Metastatic Melanoma Patients, PLOS One 2013, 8(3): e57922.

* cited by examiner

*Primary Examiner* — Michail A Belyavskyi
(74) *Attorney, Agent, or Firm* — Law Office of Darius Gleason APC

(57) ABSTRACT

Disclosed are methods and compositions useful for treating patients with inflammatory, auto-immune and age related conditions. The disclosure relates to using Natural Killer cells and derivatives thereof in order to induce therapeutic benefit to patients affected by disease and conditions such as cancer, multiple sclerosis, rheumatoid arthritis, type I diabetes mellitus, thyroid autoimmune disease, psoriasis and inflammatory bowel diseases. In some embodiments the disclosure permits physiological compensation for disease conditions by reduction of inflammatory cytokine levels in plasma and of senescent peripheral blood mononuclear cells thereby prolonging the time until medical intervention may be required. In alternate embodiments the disclosure permits physiological compensation for disease conditions by reduction of inflammatory cytokine levels in plasma and reduction of senescent peripheral blood mononuclear cells following medical intervention.

17 Claims, 9 Drawing Sheets

Study Setup
Participants, Schedule of Sample Collection and Markers Used

| Participant | Gender | Age | Known Ailments |
|---|---|---|---|
| A | Male | 39 | Irritable Bowel Syndrome - D |
| B | Male | 50 | None Relevant |
| C | Male | 70 | Advanced Age |

Schedule of sample collection for the study

| | Days Relative to NK cell injection | | | | | | |
|---|---|---|---|---|---|---|---|
| Procedure | -7 | -1 | 0 | 3 | 14 | 30 | 90 |
| NK cell infusion | | | + | | | | |
| CBC plus Homocysteine, Sedimentation rate, HS-CRP, Fibrinogen, Liver and Kidney markers | + | + | | + | + | + | + |
| Plasma collection in EDTA tubes for cytokine profiles | + | + | | + | + | + | + |
| Blood draw for isolation of PBMCs and NK cells | | | | | + | | |

FIG. 1

NATURAL KILLER CELL ADOPTIVE TRANSFER THERAPY FOR THE ELIMINATION OF SENESCENT PBMCS, REDUCTION OF INFLAMMATORY CYTOKINES AND TREATMENT OF IBS

CROSS REFERENCE TO RELATED APPLICATIONS

This application claims priority to U.S. Provisional Application No. 62/580,071 METHODS OF USING NATURAL KILLER CELLS FOR THERAPEUTIC EFFECT, the entire disclosure of which is incorporated herein by reference in its entirety.

FIELD OF INVENTION

The disclosure relates in general to cell therapy. More specifically it relates to immunotherapy and methods thereof, and to cells and compositions of matter useful for treatment of several disease conditions related to inflammation, auto-immunity and aging. More specifically the disclosure relates to methods adoptive transfer cell therapy, means of enhancing cellular therapy, and means of manipulating endogenous cells to effect therapeutic repair and recovery, and/or to delay the need for medical or surgical intervention or enhance recovery following such interventions.

BACKGROUND OF THE INVENTION

At present many diseases related to inflammation, auto-immunity and aging lack adequate and comprehensive treatment options. These diseases often culminate in severe adverse physiological effects that reduce longevity and quality of life among sufferers. This collection of conditions, referred to as "inflammaging", are thought to share molecular pathways, immune system mechanisms and underlying causative factors Inflammation is the primary mechanism used by the immune system to combat infection. Immune system cells including T cells provoke inflammation in response to recognition of surface markers on bacterial and viral pathogens. Inflammation is provoked in part by the release of cytokines that cause nearby blood vessels to dilate enabling increased local blood flow and the arrival of more immune cells to mount a defense.

In the case of cancer, inflammatory responses are critical at several points in tumor development including initiation, growth, and metastasis. The failure of the immune system to identify and respond to oncogenic cells is the essential mechanism of cancer progression. Immune cells are known to communicate extensively with cancer cells and this communication may contribute to a standing down of the immune system and other improper responses. When cancer cells spread from the primary tumor site into bone marrow the immune response is further suppressed by reduced bone marrow output of immune cell populations.

Multiple sclerosis (MS) is considered to be an autoimmune disease and is the most common immune mediated disorder affecting the central nervous system. The name refers to the numerous scars or lesions that develop on the white matter of the brain and spinal cord. In MS, inflammatory cytokines such as interleukin (IL)-12 are expressed at high levels in early forming lesions causing an increase in circulating myelin-reactive T-cells and IL-12 production. Myelin-reactive T cells also express adhesion molecules enabling their passage through the blood-brain barrier resulting in an accumulation of immune system cells in nervous system tissue. It is also thought that some regulatory T cells contribute to MS pathogenesis by exhibiting decreased activity thereby allowing immune cell invasion of neural tissue and resultant inflammation.

Rheumatoid arthritis (RA) is an auto-immune disease resulting in joint pain, stiffness and irreversible joint damage. RA poses systemic risks to other vital organs including the cardiovascular and respiratory systems. RA primarily affects the synovium or membrane lining surrounding joints which functions to protect against pathogenic infections. Typical synovial abnormalities are synovial lining cell proliferation, invasion of blood vessels into the joint, inflammatory cell infiltration and elevated levels of cytokines including tumor necrosis factor alpha (TNFα), IL-1β, and IL-8. As a result of inflammation the synovium becomes thicker and eventually results in destroyed cartilage, tendons, ligaments and bone in the joint.

Type 1 diabetes is also considered to be an autoimmune disease with wide ranging deleterious effects reaching all vital systems. Excessive calorie intake requires increased storage in fat and places increased demand on the pancreas for insulin production and upon fat cell insulin sensitivity. In adults, fat tissue expansion mostly occurs by individual fat cells increasing in size rather than by increased numbers of fat cells. Very large lipid laden cells are more prone to mechanical stress, hypoxia and cell death and this results in a continuous inflammatory state in fat tissue. Pancreatic β-islet cells are also affected by infiltration of neutrophils, B cells and locally increased levels of interferon (IFN). Over time this inflammatory state produces an accumulation of self-reactive immune cells resulting β-islet cell death, reduced insulin production and insulin sensitivity leading to hyperglycemia.

Thyroid autoimmune disease (AITD) is a common organ specific autoimmune disorder seen mostly in women. Thyroid autoimmunity occurs in several forms ranging from hypo to hyperthyroidism and has multifactorial adverse effects. Its two most prevalent forms are Hashimoto's thyroiditis and Grave's disease. Hashimoto's thyroiditis is a T cell-mediated organ specific autoimmune disease that results in thyroid destruction by infiltrating and locally activated thyroglobulin specific T cells. Whereas Grave's disease is thought to be caused by overstimulation of thyroid cells as a result of B cell antibody accumulation. Other models posit a role for activated T-lymphocytes, NK cells, and associated cytokines.

Psoriasis is among the most prevalent autoimmune diseases affecting 2-3% of the population. Characteristic symptoms of psoriasis are red, scaly patches known as plaques. The condition results from inflammatory dendritic cells releasing IL-23 and IL-12 to activate T cells which produce elevated levels of inflammatory cytokines IL-17, IFN-γ, TNF, and IL-22. These cytokines provoke increased proliferation of keratinocytes and endothelial cells resulting in lesioned psoriatic skin.

Inflammatory Bowel Disease (IBD) is an umbrella term used to describe disorders that involve chronic inflammation of the digestive tract including Crohns disease and ulcerative colitis. Both conditions usually involve severe diarrhea, abdominal pain, fatigue and weight loss. In both forms of IBD plasma and tissue concentrations of inflammatory cytokines such TNFα, IFN γ, IL-10, IL-6, and IL-8 are increased. Although the pathogenic mechanism of IBD remains incompletely understood it is generally understood to be caused by an inflammatory response in gut epithelial tissues which are exposed to a large antigenic load.

A range of other autoimmune diseases and inflammatory conditions are also probable members of the inflammaging disease category and are likely to have similar or related causative factors including systemic lupus, celiac disease, Sjögren's syndrome, ankylosing spondylitis, alopecia areata, vasculitis, and temporal arteritis.

Despite their common nexus to inflammation and the immune response each of the aforementioned conditions has been individually and separately targeted for medical intervention and treatment. As a result the treatment alternatives available form a patchwork of partially overlapping therapeutic approaches. Newer therapeutic techniques have sought to attack these disease conditions at a more systemic level by targeting elements of the immune system itself. For example monoclonal antibody therapy targeted against inflammatory cytokines such as IL-17, and TNFα have shown success in blocking migration of lymphocytes, depletion of T and B cell populations, and suppression of cytokine signaling. An alternative treatment modality involves use of immune system cells in cellular therapy, also known as adoptive transfer. Adoptive transfer of T cells was first reported to confer immunity to cancer in rodent models over 50 years ago. Adoptive T cell transfer involves the isolation of T cells from blood or bone marrow followed by concentration and/or expansion of the cells in vitro and reinfusion back into the autologous or allogeneic recipients.

Investigators have also sought to use NK cells in adoptive transfer because of their immunological potency against tumor cells. NK cells are a heterogeneous population of white blood cells distinct from T and B cells. They comprise 10-15% of circulating lymphocytes and are typically CD3− negative and CD56 positive. The most important subset are CD56 dim, CD16+, which make up 90% of NK cells in peripheral blood, while the remainder are CD56 bright, CD16− and located in secondary lymph tissue. However, development of NK cell adoptive transfer procedures has been impeded by the limited supply of viable, cytotoxic NK cells. The limited supply is due in part to the relative scarcity of NK cells in blood fractions, difficulty with in vitro expansion in feeder free systems, because of poor tolerance to cryopreservation and because of yield losses during enrichment.

NK cells are likely to play an important role in the above described inflammation related disease conditions. Although the population of NK cells increases with age, the individual effectiveness of each cell decreases over time. This dynamic leads to an accumulation of low functioning NK cells that upset homeostatic equilibrium with an attendant increase in pathogen infections and reactivation of latent infections.

RELATED ART

Bilsborough, J. et al "Therapeutic Targets in Inflammatory Bowel Disease: Current and Future." The American Journal of Gastroenterology Supplements volume 3, pages 27-37 (2016)

Ghosh, S et al. "Interfering with interferons in inflammatory bowel disease" Gut vol. 55, 8 (2006): 1071-3.

Lowes, M. A. et al. "Immunology of psoriasis" Annual review of immunology vol. 32 (2014): 227-55.

Ganesh, B. B. et al. "Role of cytokines in the pathogenesis and suppression of thyroid autoimmunity" Journal of interferon & cytokine research: the official journal of the International Society for Interferon and Cytokine Research vol. 31, 10 (2011): 721-31.

Roep, B. O. "β-Cells, Autoimmunity, and the Innate Immune System: "un Ménage á Trois"? Diabetes June 2013, 62 (6) 1821-1822;

Shao, P. et al. "Modulation of the immune response in rheumatoid arthritis with strategically released rapamycin" Molecular medicine reports vol. 16, 4 (2017): 5257-5262.

Mitchison, N. A., "Studies on the immunological response to foreign tumor transplants in the mouse. I. The role of lymph node cells in conferring immunity by adoptive transfer" Journal of experimental medicine vol. 102, 2 (1955): 157-77.

Baker, Darren J et al. "Naturally occurring p16(Ink4a)-positive cells shorten healthy lifespan" Nature vol. 530, 7589 (2016): 184-9.

Jin, Y. et al., "Mesenchymal stem cells cultured under hypoxia escape from senescence via down-regulation of p16 and extracellular signal regulated kinase", Biochem Biophys Res Commun. 2010 Jan. 15; 391(3):1471-6.

Grivennikov, Sergei I et al. "Immunity, inflammation, and cancer" Cell vol. 140, 6 (2010): 883-99. Andersen, Catherine J et al. "Impact of Obesity and Metabolic Syndrome on Immunity" Advances in nutrition (Bethesda, Md.) vol. 7, 1 66-75. 7 Jan. 2016

Steel, A. W., et al., "Increased proportion of CD16+NK cells in the colonic lamina propria of inflammatory bowel disease patients, but not after azathioprine treatment." 2011, Alimentary Pharmacology & Therapeutics, 33: 115-126. doi:10.1111/j.1365-2036.2010.04499.x Matsumoto O. S. et al "Inflammatory bowel disease-like enteritis and caecitis in a senescence accelerated mouse P1/Yit strain." Gut. 1998; 43(1):71-78.

Yadav, P. K. et al., "Potential Role of NK Cells in the Pathogenesis of Inflammatory Bowel Disease," Journal of Biomedicine and Biotechnology, vol. 2011, Article ID 348530, 6 pages, 2011. doi:10.1155/2011/348530

On M T et al. "Unlicensed" Natural Killer cells dominate the response to cytomegalovirus infection. Nature immunology. 2010; 11(4):321-327. doi:10.1038/ni.1849.

Hazeldine J, Lord J M. The impact of ageing on natural killer cell function and potential consequences for health in older adults. Ageing Research Reviews. 2013; 12(4):1069-1078. doi:10.1016/j.arr.2013.04.003.

SUMMARY OF THE INVENTION

The disclosure teaches methods and compositions of NK cells for treatment of inflammation related diseases and conditions.

In another aspect the disclosure teaches methods and compositions of NK cells for treatment of auto-immune related diseases and conditions.

In another aspect the disclosure teaches methods and compositions of NK cells for treatment of age related diseases and conditions.

In another aspect the disclosure teaches methods of using NK cells for adoptive transfer therapy.

In another aspect the disclosure teaches compositions of NK cells that are CD3 negative and CD56 positive for treatment of a range of disease and conditions including but not limited to cancer, multiple sclerosis, rheumatoid arthritis, type 1 diabetes, thyroid autoimmune disease, psoriasis, and inflammatory bowel disease.

In another aspect the disclosure teaches adoptive transfer of autologous NK cells.

In another aspect the disclosure teaches adoptive transfer of allogeneic NK cells.

In another aspect the disclosure teaches methods of treating inflammaging through administration of a therapeutically sufficient concentration a cellular preparation derived from NK cells in primary blood fractions.

In another aspect the disclosure teaches methods and compositions that induce regeneration in patients in need thereof.

In another aspect the disclosure teaches methods and compositions that suspend inflammation in patients in need thereof.

In another aspect the disclosure teaches methods and compositions that reverse inflammation in patients in need thereof.

The disclosure teaches not only methods and means of inducing regeneration, suspending inflammation and reversing inflammation prior to medical intervention but also after medical intervention to enhance the beneficial aspects of said medical intervention.

In another aspect the disclosure teaches methods and compositions for treatment of disease by adoptive transfer procedures that confer clinical improvements in blood levels of factors chosen from the group including but not limited to: Alpha-1-Antitrypsin, Alpha-2-Macroglobulin, B-2-Microglobulin, brain-derived neurotrophic factor (BDNF), C-reactive protein (CRP), complement C3, Eotaxin-1, Factor VII, Ferritin, Fibrinogen, granulocyte macrophage colony stimulating factor (GMCSF), Haptoglobin, Intercellular Adhesion Molecule 1, IFN-γ, IL-1α, IL-1β, IL1RA, IL-2, IL-3, IL-4, IL-5, IL-6, IL-7, IL-8, IL-10, IL-12, subunit p40, IL-12 subunit p70, IL-15, IL-17A, IL-18, IL-23, IL-27, macrophage inflammatory protein (MIP) 1a, MIP 1β, matrix metalloproteinase 3, (MMP-3), MMP-9, monocyte chemotactic protein (MCP 1), stem cell factor (SCF), RANTES, Tissue Inhibitor of Metalloproteinases 1, TNFα, TNFβ, tumor necrosis factor receptor 2 (TNFr2), vascular cell adhesion molecule-1 (VCAM-1), vascular endothelial growth factor (VEGF), Vitamin D-Binding Protein, von Willebrand Factor, B-Galactosidase.

In another aspect disclosure teaches methods and compositions for treatment of disease by adoptive transfer procedures that confer clinical improvement in blood levels of factors chosen from the group but not limited to cytokines IFNγ, IL-6; IL-17A, IL-27, MCP-1.

In another aspect the disclosure teaches methods and compositions for treatment of disease by adoptive transfer procedures that confer clinical improvement in peripheral blood mononuclear cell concentration of factors chosen from the group but not limited to: p16 and p21.

In another aspect the disclosure teaches methods and compositions for treatment of disease by adoptive transfer procedures that confer clinical improvement in peripheral blood mononuclear cell concentration of cyclin dependent kinase inhibitors.

The present invention achieves its objects by providing compositions and methods for adoptive transfer of NK cells for treatment of patients with inflammatory, auto-immunity and age related conditions. The manners in which the invention achieves its objects and other objects which are inherent in the invention will become more readily apparent when reference is made to the figures and detailed description of the invention.

FIGURES

FIG. 1 details the study design.

DETAILED DESCRIPTION OF THE PREFERRED EMBODIMENT

Figure 2:
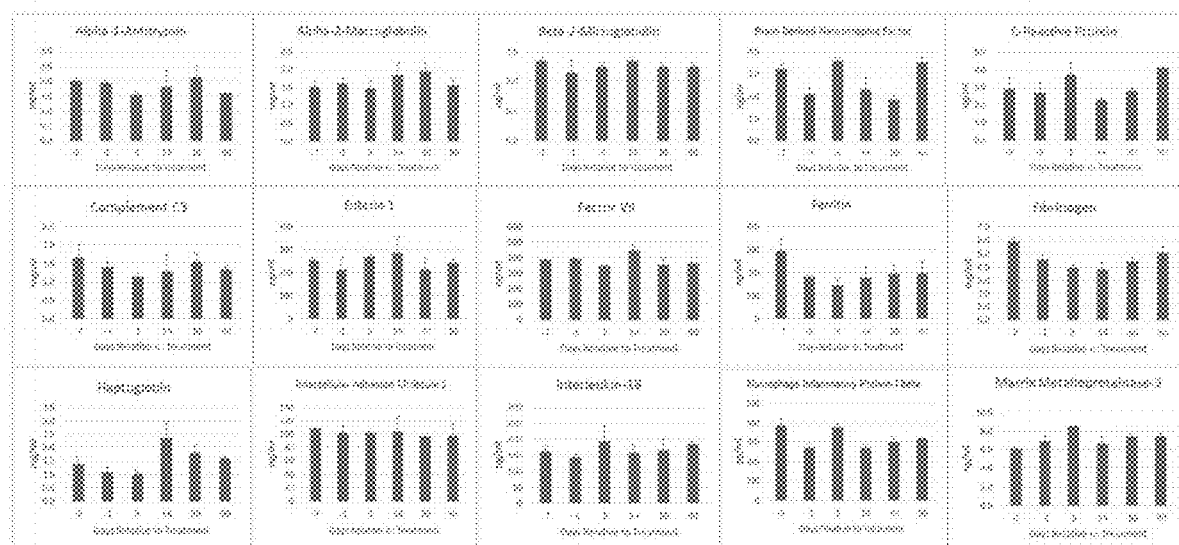
FIG. 2 depicts the results of cytokine determination in plasma of donor A before and after NK cell treatment.

Various embodiments of the invention are described in detail and may be further illustrated by the provided examples. As used in the description herein and throughout the claims that follow, the meaning of "a," "an," and "the" includes the plural reference unless the context clearly dictates otherwise. Also, as used in the description herein, the meaning of "in" includes "in" and "on" unless the context clearly dictates otherwise. Throughout this specification and claims, the word "comprise," or variations such as "comprises" or "comprising" will be understood to imply the inclusion of a stated integer or group of integers but not the exclusion of any other integer or group of integers. Terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms does not exclude the use of other synonyms. The use of examples anywhere in this specification, including examples of any terms discussed herein, is illustrative only, and in no way limits the scope of the invention so long as the data are processed, sampled, converted, or the like according to the invention without regard for any particular theory or scheme of action. The entire contents of all the references (including literature references, issued patents, published patent applications, and co-pending patent applications) cited throughout this application are hereby expressly incorporated by reference.

The use of NK cells in treatment of inflammation, auto-immunity and aging may take many embodiments and the description provided herein is only meant to be illustrative of some of the embodiments. One skilled in the art will realize that numerous modifications, concentrations, and additives may be used in the context of practicing the current invention without departing from the spirit of the teachings herein.

In one embodiment human NK cells, CD3 negative and CD56 positive, were isolated from peripheral blood of three donors (Samples A, B and C) using a standard protocol. In the embodiment, cells were frozen at a concentration of 2×10^7/ml in CryoStor CS10 Freeze Medium but in other embodiments could be frozen at other concentrations and in other mediums. Prior to injection the cells were thawed and suspended in FRS Hypothermic Preservation medium for transfer to the intravenous infusion site, though other media could be used in alternate embodiments. In this embodiment the size of the injection was 1 billion cells but in other embodiments could be a more or fewer cells. In this embodiment plasma samples were analyzed for the following cytokines using Myriad RBM services or Affymetrix ELISA kits: Alpha-1-Antitrypsin, Alpha-2-Macroglobulin, B-2-Microglobulin, brain-derived neurotrophic factor (BDNF), C-reactive protein (CRP), complement C3, Eotaxin-1, Factor VII, Ferritin, Fibrinogen, granulocyte macrophage colony stimulating factor (GMCSF), Haptoglobin, Intercellular Adhesion Molecule 1, IFN-γ, IL-1α, IL-1β, IL1RA, IL-2, IL-3, IL-4, IL-5, IL-6, IL-7, IL-8, IL-10, IL-12, subunit p40, IL-12 subunit p'70, IL-15, IL-17A, IL-18, IL-23, IL-27, macrophage inflammatory protein (MIP) 1a, MIP 1β, matrix metalloproteinase 3, (MMP-3), MMP-9, monocyte chemotactic protein (MCP 1), stem cell factor (SCF), RANTES, Tissue Inhibitor of Metalloproteinases 1, TNFα, TNFβ, tumor necrosis factor receptor 2 (TNFr2), vascular cell adhesion molecule-1 (VCAM-1), vascular endothelial growth factor (VEGF), Vitamin D-Binding Protein, von Willebrand Factor, p16, p21, B-Galactosidase. In related or alternate embodiments other cytokines and cellular markers could be assayed.

Cytokines were assayed at 6 time points (FIG. 2) including at two points, seven and one day, prior to NK adoptive transfer and four time points, three, fourteen thirty and ninety days, following adoptive transfer. Among the assayed markers, IL-6 is a cytokine released by leukocytes in response to inciting stimuli. In addition to its role as an acute phase reactant and endogenous pyrogen, IL-6 is also involved in B-cell differentiation into plasma cells. IFNγ is activating to macrophages and increases the expression of class II MHC on antigen presenting dendritic cells. IL-17 recruits monocytes and neutrophils to inflammation sites by increasing chemokine production in various tissues. IL-27 is involved in the pathogenesis of IBD and is often found to be upregulated in affected patients. MCP-1 plays a role in the recruitment of monocytes to sites of injury and infection. Cyclin dependent kinase inhibitors p16 and p21 were assayed at two time points, sixty five days prior to NK cell adoptive transfer and fourteen days after transfer. P16, also known as P16$^{INK4a}$ is a tumor suppressor gene which prohibits progression from G1 to S phase of the cell cycle. P16 is an aging biomarker because it is frequently expressed by senescent cells. P21, also known as P21$^{CIP1}$ is a major target of tumor suppressor gene p53 and is associated with cell cycle arrest in DNA damaged cells. P21 is similarly found at elevated levels in the PBMCs of older human patients.

EXAMPLES

Example 1: Donor with IBS Symptoms

Figure 3:
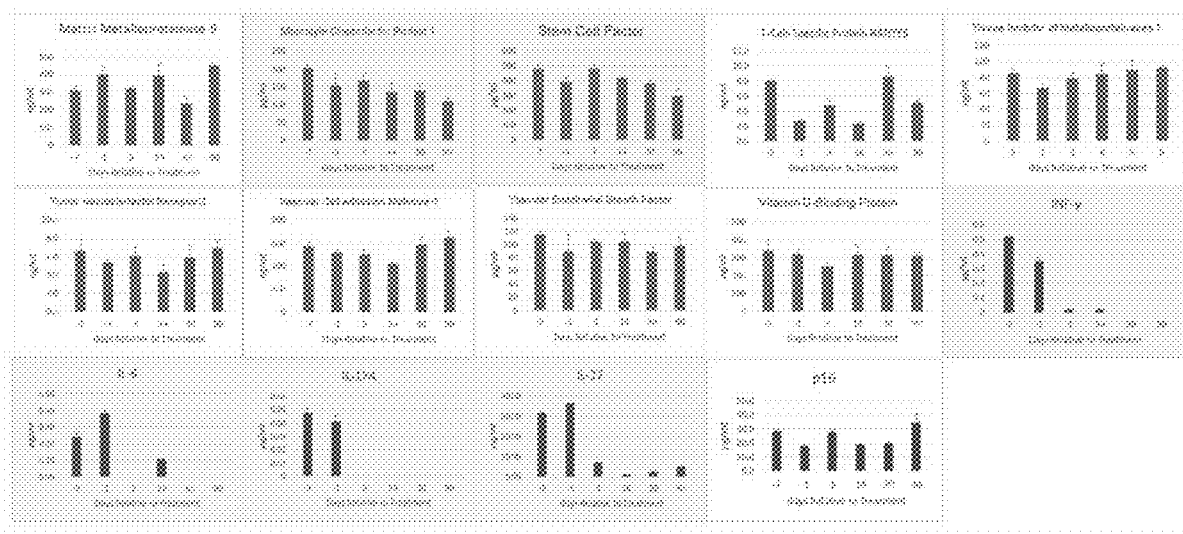
FIG. 3 depicts additional results of cytokine determination in plasma of donor A before and after NK cell treatment.

FIGS. 2 and 3 show the effects of autologous NK adoptive transfer in donor A, a 39 year old male with irritable bowel syndrome. Donor A experienced stomach pain and diarrhea prior to autologous NK cell adoptive transfer. Donor A also exhibited elevated IL-6 levels before the adoptive transfer (FIG. 3), IL-6 is usually not detected in normal serum, plasma, CSF, or joint fluid, and this indicates ongoing initial inflammatory processes correlating with the clinical diagnosis of Irritable Bowel Syndrome (IBD). Following infusion Donor A experienced elimination of IBS symptoms correlated by significant down regulation in plasma levels of IFNγ, IL-6, IL-17A, and IL-27. The observed decline in IFNγ production indicates that inflammation, or its underlying causes, no longer stimulate its production by T cells (cytotoxic and Th1) and by NK cells. The observed reduction in IL-27 levels similarly indicates suppression of inflammation in intestinal tissues. Donor A also exhibited a decrease in MCP-1 consistent with reduced monocyte infiltration and inflammation. Assays of expression in peripheral blood mononuclear cells (FIGS. 8-9) showed significant reduction of both p16 and p21 which are associated with cellular senescence. The results indicate that autologous NK cell adoptive transfer into a patient with a preexisting inflammatory condition dramatically reduced inflammatory cytokines in blood plasma as well as eliminating senescent PBMCs.

Example 2: Asymptomatic Donor

Figure 4:
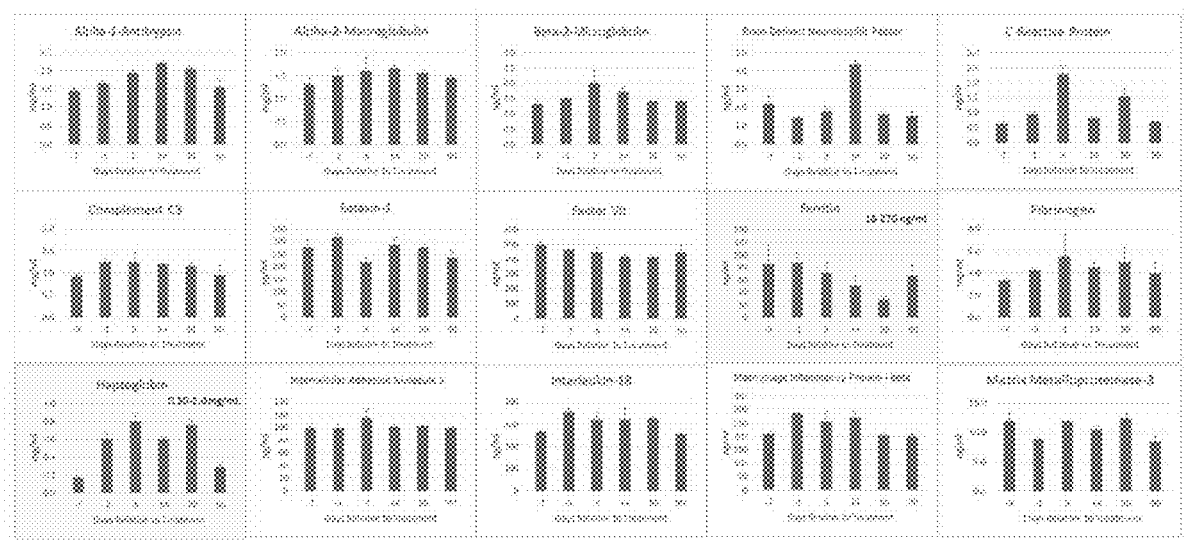
FIG. 4 depicts the results of cytokine determination in plasma of donor B before and after NK cell treatment.
Figure 5:
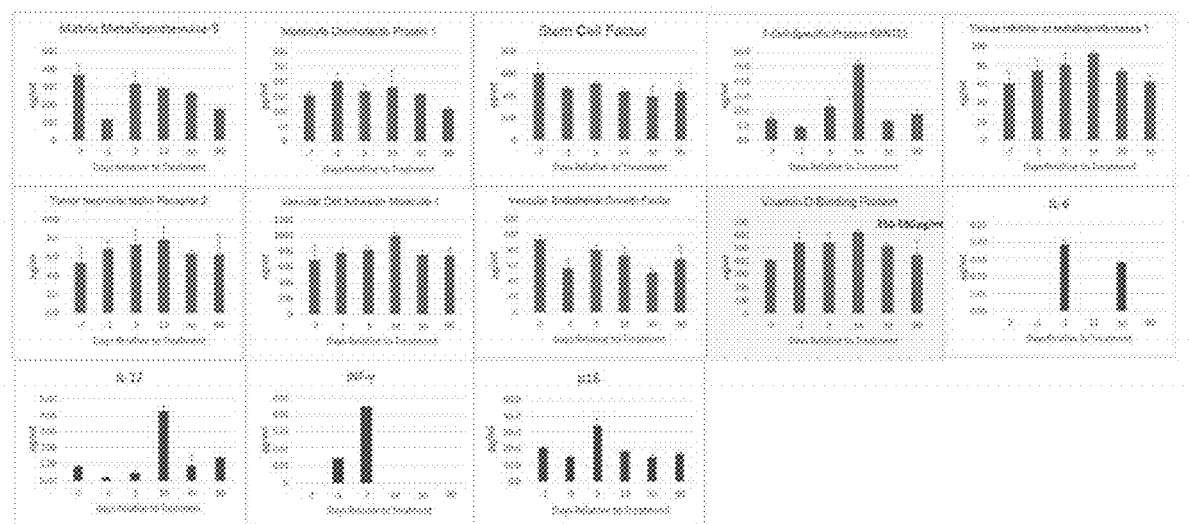
FIG. 5 depicts additional results of cytokine determination in plasma of donor B before and after NK cell treatment.

FIGS. 4 and 5 show the effects of autologous NK adoptive transfer in donor B, a 50 year old male with no known ailments or targets of NK cell cytotoxicity. Given his overall health and lack of preexisting inflammation the cytokine assays predictably show a lack of inflammation prior to adoptive transfer and no pronounced reduction in inflammatory factors following the transfer. Donor B did however exhibit non-significant decreases in MPC-1 and SCF consistent with the results observed in Donor A. Donor B also exhibited significant reductions in p16 and p21 concentrations in PBMCs (FIGS. 8-9) indicating that senescent PBMCs were eliminated by the adoptive transfer therapy.

Example 3: Geriatric Donor

Figure 6:
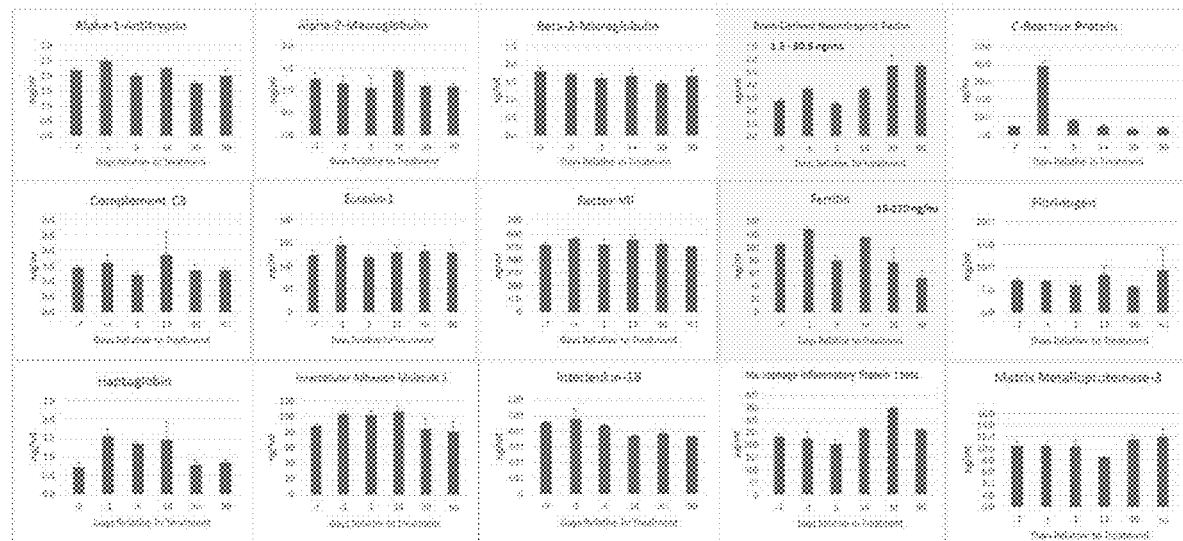
FIG. 6 depicts the results of cytokine determination in plasma of donor C before and after NK cell treatment.
Figure 7:
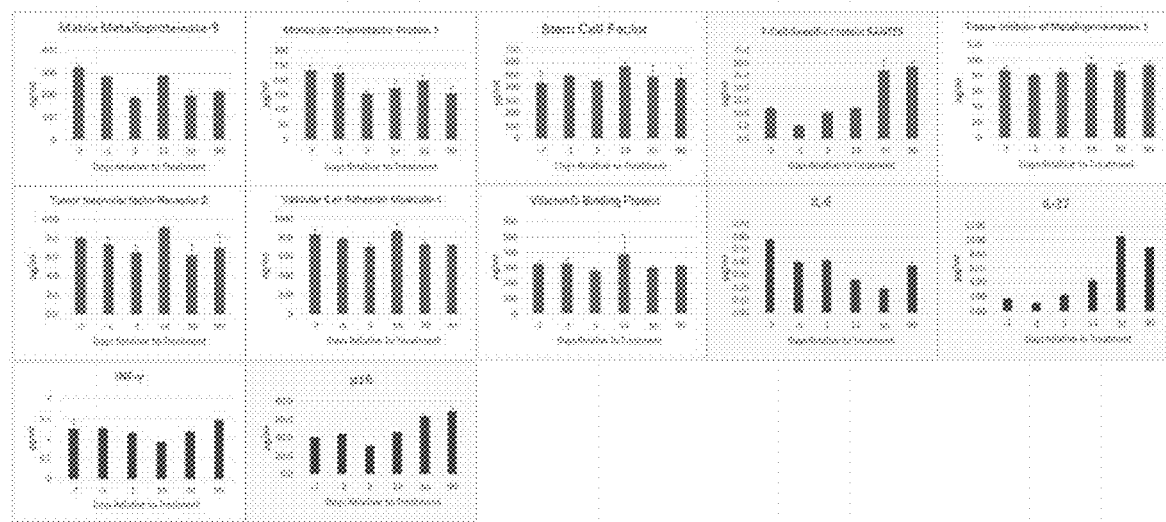
FIG. 7 depicts additional results of cytokine determination in plasma of donor C before and after NK cell treatment.
Figure 8:
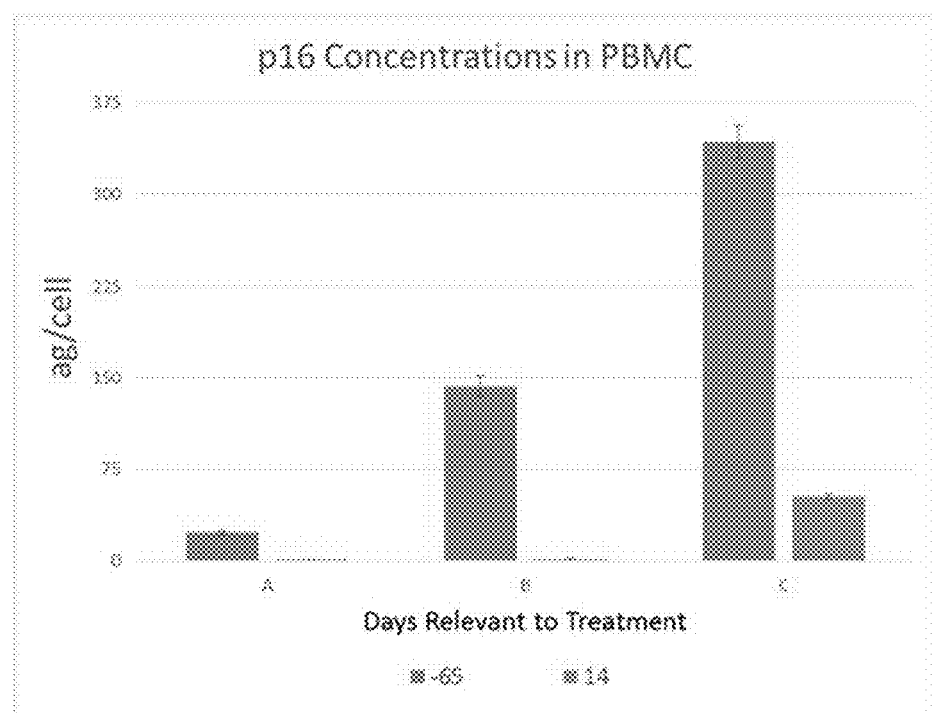
FIG. 8 depicts the results of p16 determination in PBMC before and after NK cell treatment in all three donors.
Figure 9:
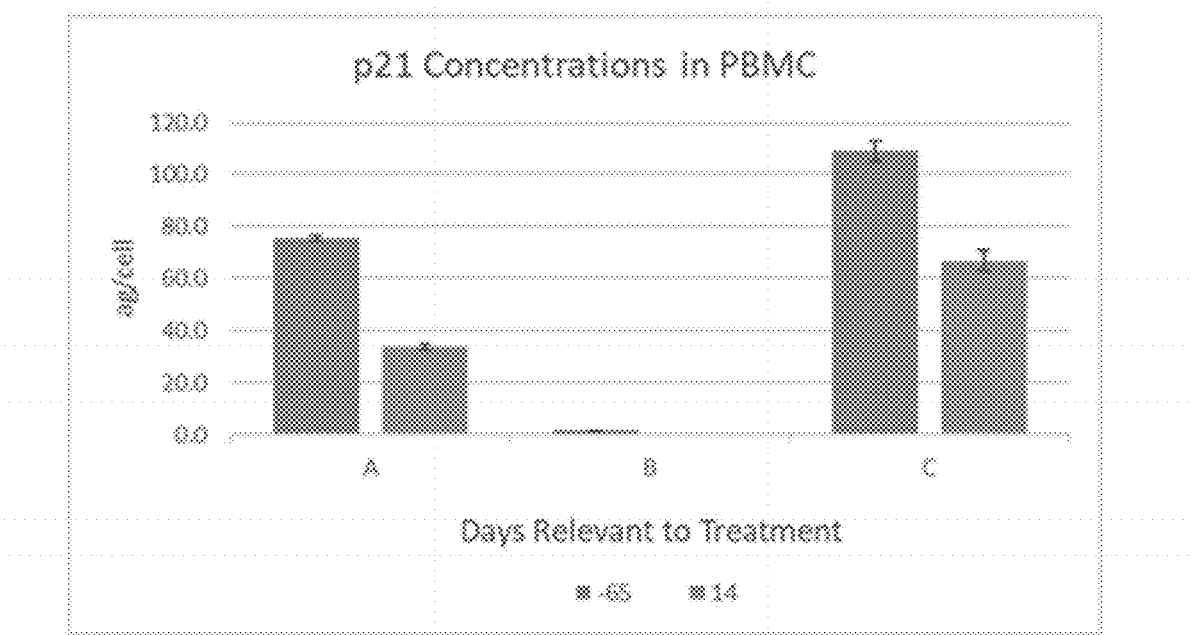
FIG. 9 depicts the results of p21 determination in PBMC before and after NK cell treatment in all three donors.

FIGS. 6 and 7 show the effects of autologous NK cell adoptive transfer in Donor C, a 70 year old male. Donor C is the oldest in the cohort which accounts for the high levels of PBMC p16 and p21 concentration prior to adoptive transfer. Following the therapy Donor C exhibited significant reductions in p16 and p21 concentrations in PBMCs (FIGS. 8-9). A significant reduction in plasma levels of IL-6 is also noted. IL-6 exhibits a steady decline after NK cell treatment followed by a recovery after 90 days indicating an anti-inflammatory effect from the adoptive transfer. Donor C also exhibited non-significant decreases in MCP-1 also substantiating the conclusion that NK cell adoptive transfer reduces inflammation.

One skilled in the art will appreciate that these methods, compositions, and cells are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention. Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suit ably may be practiced in the absence of any element or elements, limitation or limitations which is not specifically disclosed herein. Thus, for example, in each instance herein any of the terms "comprising." "consisting essentially of and "consisting of may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be under stood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure. Those skilled in the art will recognize, or be able to ascertain using no more than routine experimentation, many equivalents of the specific embodiments of the invention described herein. Such equivalents are intended to be encompassed by the following claims.

What is claimed:

1. An adoptive transfer procedure for treating inflammatory bowel disease comprising:
   a) Isolating natural killer (NK) cells that are CD3 negative and CD56 positive from peripheral blood of a human donor;
   b) Expanding said NK cells in vitro;
   c) Intravenously infusing said NK cells into said donor.

2. The method of claim 1 further comprising the step of cryopreserving said NK cells.

3. The method of claim 2 further comprising the step of thawing said cryopreserved NK cells prior to infusion.

4. The method of claim 1 wherein said adoptive transfer is administered to a human without any form of cancer.

5. The method of claim 1 wherein said adoptive transfer is administered to a human without any need for antiviral treatment.

6. An adoptive transfer procedure for eliminating senescent peripheral blood mononuclear cells comprising:
   a) Isolating NK cells from a that are CD3 negative and CD56 positive from peripheral blood of a human donor;
   b) Expanding said NK cells in vitro;
   c) Intravenously infusing said NK cells into said donor.

7. The method of claim 6 wherein said NK cells are CD3 negative and CD56 positive.

8. The method of claim 6 wherein said infusion is autologous.

9. The method of claim 6 further comprising the step of cryopreserving said NK cells.

10. The method of claim 9 further comprising the step of thawing said cryopreserved NK cells prior to infusion.

11. The method of claim 6 wherein said adoptive transfer is administered to a human without any form of cancer.

12. The method of claim 6 wherein said adoptive transfer is administered to a human without any need for antiviral treatment.

13. An adoptive transfer procedure for reducing blood plasma levels of inflammatory cytokines comprising:
    a) Isolating NK cells that are CD3 negative and CD56 positive from peripheral blood of a human donor;
    b) Expanding said NK cells in vitro;
    c) Intravenously infusing said NK cells into said donor.

14. The method of claim 13 further comprising the step of cryopreserving said NK cells.

15. The method of claim 14 further comprising the step of thawing said cryopreserved NK cells prior to infusion.

16. The method of claim 13 wherein said adoptive transfer is administered to a human without any form of cancer.

17. The method of claim 13 wherein said adoptive transfer is administered to a human without any need for antiviral treatment.

* * * * *